US00PP16857P3

(12) United States Plant Patent
Bernuetz

(10) Patent No.: US PP16,857 P3
(45) Date of Patent: Jul. 25, 2006

(54) ***ARGYRANTHEMUM* PLANT NAMED 'OHMADLEVA'**

(50) Latin Name: *Argyranthemum×hydrida*
Varietal Denomination: OHMADLEVA

(75) Inventor: Andrew Bernuetz, Silverdale (AU)

(73) Assignee: Bonza Botanicals Pty., Ltd., Sydney (AU)

( * ) Notice: Subject to any disclaimer, the term of this patent is extended or adjusted under 35 U.S.C. 154(b) by 118 days.

(21) Appl. No.: 11/011,335

(22) Filed: Dec. 13, 2004

(65) Prior Publication Data

US 2006/0130200 P1 Jun. 15, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Buchanan Ingersoll PC

(57) ABSTRACT

A new and distinct cultivar of *Argyranthemum* plant named 'OHMADLEVA' characterized by its single inflorescence form with white-colored ray florets, yellow-colored disc florets, freely branching character, dark green-colored foliage, and compact and upright growth habit.

1 Drawing Sheet

Latin name of the genus and species of plant claimed: *Argyranthemum×hybrida.*
Variety denomination: 'OHMADLEVA'.

BACKGROUND OF THE INVENTION

The present invention relates to a new and distinct cultivar of *Argyranthemum* plant botanically known as *Argyranthemum×hybrida,* and hereinafter referred to by the cultivar name 'OHMADLEVA'.

The new *Argyranthemum* originated in a controlled breeding program in Winmalee, New South Wales, Australia during 2001. The objective of the breeding program was the development of *Argyranthemum* cultivars that are freely branching, have a compact and upright growth habit, are freely flowering, and have unique flower coloration.

The female (seed) parent of the new cultivar was the proprietary breeding line 01-103, not patented, which exhibits a medium growth habit. The male (pollen) parent of the new cultivar was proprietary breeding line 01-253, not patented, which exhibits double flower form and light yellow-colored ray florets. Seed from the above stated cross-pollination was germinated and grown to maturity. One plant within the progeny was discovered and selected by the inventor on Sep. 24, 2002 in a controlled environment at Winmalee, New South Wales, Australia.

Asexual reproduction of the new cultivar by terminal stem cuttings since September 2002 at Winmalee, New South Wales, Australia and West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'OHMADLEVA' as a new and distinct cultivar of *Argyranthemum* plant.

1. Single inflorescence form with white-colored ray florets and yellow-colored disc florets.

2. Dark green-colored foliage.
3. Freely branching character.
4. Compact and upright growth habit.

Plants of the new cultivar differ from plants of the female parent primarily in growth habit and from the male parent primarily in flower form and flower color.

Plants of the new cultivar are similar to the cultivar Sugar Baby, U.S. Plant Pat. No. 10,298. However, in side-by-side comparisons, carried out at West Chicago Ill., plants of the new cultivar differ from plants of 'Sugar Baby' in the following characteristics:

1. Plants of the new cultivar have slightly larger flowers than plants of 'Sugar Baby'.
2. The foliage of the new cultivar is a darker green color than the foliage of 'Sugar Baby'.
3. The disc florets of the new cultivar are a darker yellow color than those of 'Sugar Baby'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of the new cultivar. The plants were grown for 13 weeks in 10 cm pots in a greenhouse at West Chicago, Ill.

DETAILED BOTANICAL DESCRIPTION

Figure 1:
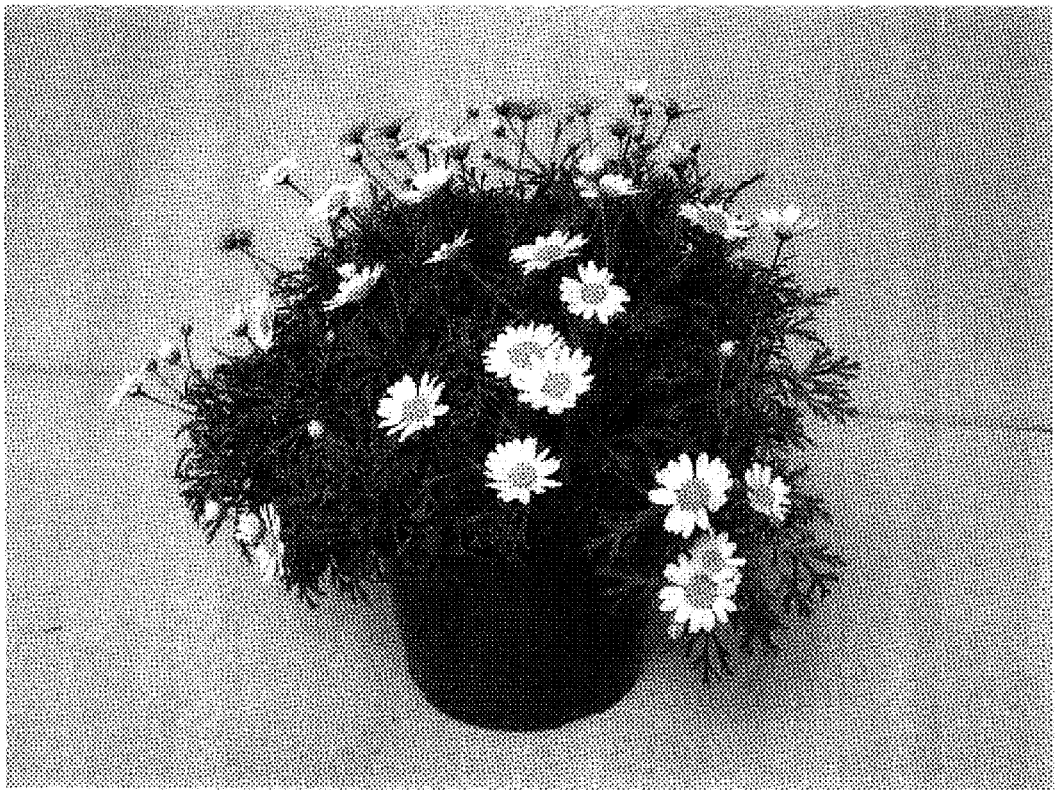
FIG. 1 illustrates a side view of the overall growth and flowering habit of 'OHMADLEVA' with one plant per pot.
Figure 2:
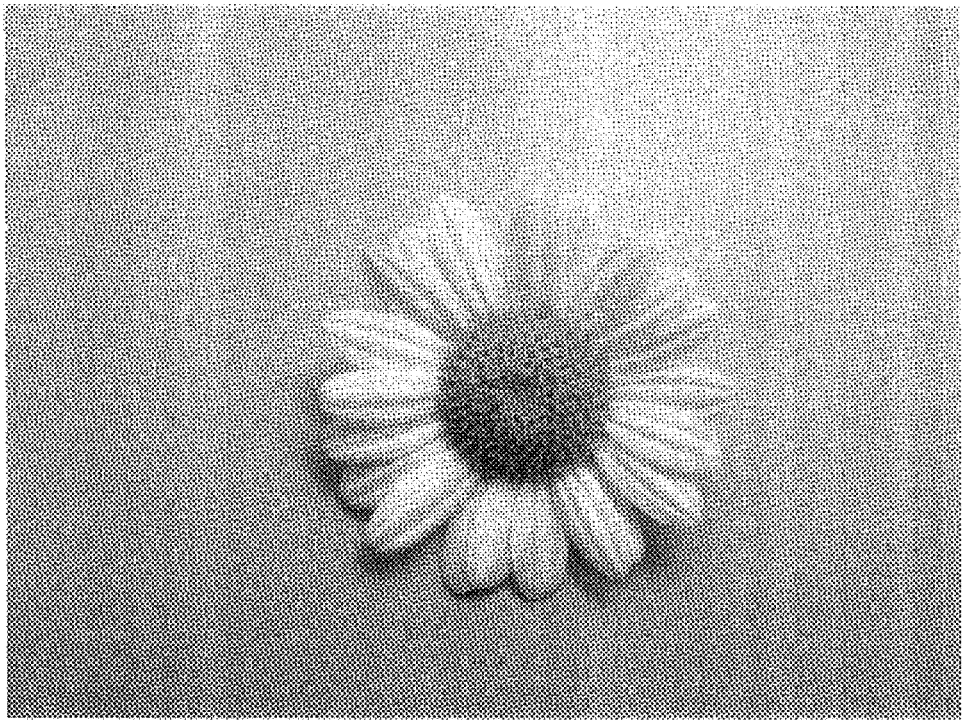
FIG. 2 illustrates a close-up view of an individual flower of 'OHMADLEVA'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is the R.H.S. Colour Chart of The Royal Horticultural Society, London, England, 2001 edition, except where color terms of ordinary significance are used. The color values were determined on Sep. 22, 2004 between 9:00 and 11:00 a.m. under natural light conditions.

The following descriptions and measurements describe plants produced from cuttings taken from stock plants and grown at West Chicago, Ill. in a double polycarbonate-covered greenhouse under conditions comparable to those used in commercial practice. The plants were grown in 10 cm pots for 13 weeks while utilizing a soilless growth medium. Greenhouse temperatures were maintained at approximately 65°–78° F. (18°–25° C.) during the day and approximately 50°–60° F. (10°–15° C.) during the night. Greenhouse light levels were maintained at 6,000 to 9,000 footcandles during the day.

Botanical classification: *Argyranthemum×hybrida* cultivar OHMADLEVA.

Parentage:

*Male parent.*—Proprietary *Argyranthemum* breeding line 01-253, not patented.

*Female parent.*—Proprietary *Argyranthemum* breeding line 01-103, not patented.

Propagation:

*Type cutting.*—Terminal stem.

*Time to initiate roots.*—Approximately 6 to 8 days.

*Time to produce a rooted cutting.*—Approximately 21 to 28 days.

*Root description.*—Fibrous.

*Rooting habit.*—Freely branching.

Plant description:

*Crop time.*—Approximately 6 to 9 weeks from a rooted cutting in a 10 cm pot.

*Habit of growth.*—Compact. Freely branching. One or two pinches improves basal branching.

*Form.*—Upright, mounded.

*Size.*—Height: Approximately 18.8 cm from soil level to top of plant plane. Width (area of spread): Approximately 28 cm.

*Branch.*—Quantity per plant: Approximately 5. Strength: Strong. Length from soil level to base of peduncle: Approximately 10.5 cm. Diameter: Approximately 3.0 mm. Appearance: Glaucous. Texture: Glabrous. Color: Young and supple: 144A, mature and woody: 199B. Internode length at middle of branch: Approximately 7.0 mm.

*Foliage.*—Quantity of leaves per branch: Approximately 15. Fragrance: Slight. Type: Simple. Arrangement: Alternate. Aspect: At an acute angle to the stem. Shape: Obovate. Apex: Narrow acute, cuspidate. Base: Attenuate, decurrent. Margin: Parted. Venation pattern: Pinnate. Length: Approximately 4.3 cm. Width: Approximately 3.2 cm. Texture: Upper and lower surfaces are glabrous. Color of young and mature foliage: Upper surface: Closest to 137A with venation of N144C, glaucous. Lower surface: 137B with venation of N144C.

Flowering description:

*Flowering habit.*—Freely flowering under outdoor growing conditions with substantially continuous blooming from spring through autumn and year round in greenhouse environment.

Inflorescence description:

*Appearance.*—Single composite form. Persistent. Shape: Round. Aspect: Facing upward or outward. Disc and ray florets develop acropetally on a capitulum. Fragrance: None.

*Quantity of flowers and buds per lateral branch.*—Approximately 2 buds and 2 open flowers.

*Size.*—Diameter: Approximately 3.5 cm. Depth: Approximately 8.0 mm.

*Lastingness of inflorescence.*—Approximately 7–10 days.

*Bud.*—Rate of opening: It takes approximately 3–6 days for buds to progress from first color to fully open flowers. Shape: Ovoid. Diameter: Approximately 6.2 mm. Depth: Approximately 4.8 mm. Color: 150C.

*Ray florets.*—Quantity per inflorescence: Approximately 21, arranged in a single whorl. Aspect: Initially upright progressing to flat at maturity. Arrangement: Imbricate at base. Shape: Oblong. Margin: Entire. Apex: Emarginate with three tips. Base: Attenuate and fused to form tube. Length: Approximately 1.5 cm. Width: Approximately 4.5 mm. Texture: Glabrous and ribbed. Color of young and mature ray florets: Upper and lower surfaces: 155A. Tube texture: Sessile glandular. Glands color: Colorless and translucent. Tube color: 144C.

*Disc.*—Diameter: Approximately 1.3 cm. Depth: Approximately 9.0 mm.

*Receptacle.*—Shape: Cone. Diameter at base: 3.9 mm. Depth: 4.9 mm. Color: 145A.

*Disc florets.*—Quantity per inflorescence: Approximately 178. Shape: Tubular with five lobes each having an acute apex. Length: Approximately 5 mm. Diameter at apex: Approximately 1.4 mm. Diameter at base: Approximately 0.5 mm. Texture: Glabrous. Color: Immature: 15B. Mature: 17A. Calyx: Shape: Tubular. Length: Approximately 2.2 mm. Diameter: Approximately 0.1 mm. Texture: Glabrous, papery. Color: Colorless, translucent.

*Phyllaries.*—Quantity per inflorescence: Approximately 14. Arrangement: Imbricate, arranged in several rows. Shape: Lanceolate. Apex: Acute. Base: Truncate. Margin: Entire. Length: Approximately 4.0 mm. Width: Approximately 1.4 mm. Texture: Glabrous, papery along edges. Color of upper and lower surface: Closest to 144B.

*Peduncle.*—Strength: Strong, pliable. Aspect: Erect. Length: Approximately 5.4 cm. Diameter: Approximately 0.8 mm. Texture: Glabrous. Color: 146A, glaucous.

*Reproductive organs.*—Androecium: Present on disc florets only. Stamens: 4. Anther length: Approximately 0.8 mm. Anther color: 22A. Amount of pollen: Moderate. Pollen color: 14A. Gynoecium: Present on ray and disc florets. There is one pistil per floret. Pistil length: 3.8 mm. Stigma shape: Two parted. Stigma length: 0.9 mm. Stigma color: 17A. Style length: 2 mm. Style color: 12B at distil end, 145A at proximal end. Ovary diameter: 0.9 mm. Ovary color: 144C.

Seed and fruit production: Neither seed nor fruit production has been observed.

Disease and pest resistance: Resistance to pathogens and pests common to *Argyranthemum* has not been observed.

What is claimed is:

1. A new and distinct cultivar of *Argyranthemum* plant named 'OHMADLEVA', substantially as herein shown and described.

* * * * *